US008197832B2

(12) United States Patent
Awakura et al.

(10) Patent No.: US 8,197,832 B2
(45) Date of Patent: Jun. 12, 2012

(54) METHODS AND COMPOSITIONS FOR INHIBITING MYCOTOXIN CONTAMINATION IN CEREALS (75) Inventors: Daisuke Awakura, Kitahiroshima (JP); Kiyoshi Kimura, Kitahiroshima (JP); Kazuyoshi Masuda, Kitahiroshima (JP)

(73) Assignees: Mitsui Chemicals Agro, Inc., Minato-Ku, Tokyo (JP); Hokusan Co., Ltd., Hokkaido (JP)

( * ) Notice: Subject to any disclaimer, the term of this patent is extended or adjusted under 35 U.S.C. 154(b) by 1034 days.

(21) Appl. No.: 10/537,117

(22) PCT Filed: Dec. 4, 2003

(86) PCT No.: PCT/JP03/15543
§ 371 (c)(1),
(2), (4) Date: Jul. 1, 2005

(87) PCT Pub. No.: WO2004/049805
PCT Pub. Date: Jun. 17, 2004

(65) Prior Publication Data
US 2006/0040030 A1   Feb. 23, 2006

(30) Foreign Application Priority Data
Dec. 4, 2002  (JP) .................. 2002-352697

(51) Int. Cl.
A01N 25/00   (2006.01)
A23L 3/34    (2006.01)
(52) U.S. Cl. ....................... 424/405; 426/532
(58) Field of Classification Search .......... 424/405; 426/532
See application file for complete search history.

(56) References Cited

U.S. PATENT DOCUMENTS

| | | |
|---|---|---|
| 2,663,628 A | 12/1953 | Thomsen |
| 3,941,896 A | 3/1976 | Smith et al. |
| 4,075,324 A | 2/1978 | Thizy et al. |
| 4,119,724 A | 10/1978 | Thizy et al. |
| 4,139,616 A | 2/1979 | Ducret et al. |
| 4,334,905 A | 6/1982 | Wagner et al. |
| 4,542,023 A | 9/1985 | Lacroix et al. |
| 4,661,477 A * | 4/1987 | Gorog nee Privitzer et al. ................. 514/76 |
| 4,698,334 A | 10/1987 | Horriere et al. |
| 4,780,458 A | 10/1988 | Hodakowski et al. |
| 4,806,445 A | 2/1989 | Horriere et al. |
| 4,849,219 A * | 7/1989 | Staub et al. ................. 424/605 |
| 4,866,043 A * | 9/1989 | Csutak et al. ................. 514/75 |
| 4,935,410 A | 6/1990 | Barlet |
| 5,070,083 A | 12/1991 | Barlet |
| 5,124,344 A | 6/1992 | Greiner et al. |
| 5,133,891 A | 7/1992 | Barr et al. |
| 5,169,646 A | 12/1992 | Horriere et al. |
| 5,206,228 A | 4/1993 | Collins |
| 5,246,953 A | 9/1993 | Greiner et al. |
| 5,290,791 A * | 3/1994 | Greiner et al. ................. 514/383 |
| 5,514,200 A | 5/1996 | Lovatt |
| 5,707,418 A | 1/1998 | Hsu |
| 5,736,164 A | 4/1998 | Taylor |
| 5,800,837 A | 9/1998 | Taylor |
| 5,830,255 A | 11/1998 | Lovatt |
| 5,865,870 A | 2/1999 | Hsu |
| 5,925,383 A | 7/1999 | Taylor |
| 5,997,910 A | 12/1999 | Taylor |
| 6,113,665 A | 9/2000 | Lovatt |
| 6,139,879 A | 10/2000 | Taylor |
| 6,168,643 B1 | 1/2001 | Hsu |
| 6,338,860 B1 | 1/2002 | Taylor |
| 6,509,041 B2 | 1/2003 | Taylor |
| 6,645,268 B2 | 11/2003 | Lovatt |
| 6,896,714 B2 | 5/2005 | Lovatt |
| 6,929,673 B1 | 8/2005 | Lovatt |
| 7,160,349 B2 | 1/2007 | Lovatt |
| 7,160,350 B2 | 1/2007 | Lovatt |

FOREIGN PATENT DOCUMENTS

| | | |
|---|---|---|
| DE | 3417133 A1 | 11/1985 |
| EP | WO 8600613 A1 | 1/1986 |
| EP | 0467792 | 1/1992 |
| FR | 2359077 A1 | 7/1978 |
| FR | 2389587 A1 | 12/1978 |
| GB | 2279252 | 1/1995 |
| JP | 61 291482 A | 12/1986 |
| JP | 62-87504 A | 4/1987 |
| JP | 474784 A | 3/1992 |
| JP | 07-223913 | 8/1995 |
| JP | 7-223913 A | 8/1995 |
| JP | 2002-255704 | 9/2002 |
| JP | 2002-348203 A | 12/2002 |
| JP | 62-87504/1987 | 1/2009 |
| RU | 655373 A1 | 4/1979 |
| WO | WO 9819544 | 5/1998 |
| WO | WO 9953761 | 10/1999 |
| WO | WO 0046169 | 8/2000 |
| WO | WO 02076215 | 10/2002 |

OTHER PUBLICATIONS

Pirgozliev et. al. (European Journal of Plan Pathology (2002) 108:469-478).*

(Continued)

Primary Examiner — Marcos Sznaidman
(74) Attorney, Agent, or Firm — Buchanan Ingersoll & Rooney PC (57) ABSTRACT We search for a cultivation method for reducing the amount of mycotoxin contamination in wheat which has been an important pending question for the quality in actual producing field of wheat and the health hazard risk for customers.

The present invention discloses a method of reducing the contamination amount of mycotoxin in cereals characterized in that one or more compounds A selected from the group consisting of ammonium salts, primary to quaternary ammonium salts, alkali metal salts, alkaline earth metal salts and polyvalent metal salts of phosphorous acid and phosphite ester are given to the cereals.

5 Claims, 2 Drawing Sheets

OTHER PUBLICATIONS

Davis et. al. (Plant Pathology (1994) 43:200-205).*
"Hokkaido no Hatasaku Gijutu—Mugirui Hen—(Farming Technology in Hokkaido—Cereals version-)", published by Nogyo Gijyutsu Fukyu Kyokai (Society for Agricultural Technique Propagation), p. 209 (1978).
"Nippon Shokubutsu Byogai Daijiten (Plant Diseases in Japan)", published by Zenkoku Noson Kyoiku Kyokai (Association for National Farming Village Education), p. 74-75 (1998).
Noyaku Hando Bukku 2001nen Ban (Agricultural Chemical Handbook, 2001 version), published by Nippon Shokubutsu Boeki Kyokai (Japan Plant Protection Association), p. 274-296 and 312-338 (2001).
Bai, G-H, et al. "Relationship between Visual Scab Ratings and Deoxynivalenol in Wheat Cultivars" The 1998 National *Fusarium* Head Blight Forum, Chapter 2, pp. 21-23 (1998).
Leroux, P et al. "Fongicides utilises en viticulture et mycotoxines" Phytoma. La Defense des Vegetaux, No. 553, Oct. 2002, p. 28-31.
Homdork, S. et al. "Effects of Field Application of Tebuconazole on Yield, Yield Components and the Mycotoxin Content of *Fusarium*-infected Wheat Grain" J. Phytopathology, vol. 148, pp. 1-6 (200).
Ellner, F. M. "Influence of Fungicide Treatment on Deoxynivalenol Content in Winter Wheat Artificially Infected with *Fusarium culmorum*" Cereal Research Communications, vol. 25, No. 3/2, pp. 735-737 (1997). Retrieved from STN Database accession No. 1997:766745.
Guest, D. et al. "The Complex Action of Phosphonates as Antifungal Agents" Biological Reviews, vol. 66, pp. 159-187 (1991).
Rickard, David A. "Review of Phosphorus Acid and Its Salts as Fertilizer Materials" J. Plant Nutrition, vol. 23, No. 2, pp. 161-180 (2000).
Davis, et al. "The effect of phosphonate on the sporulation of *Fusarium oxysporum* f.sp. *cubense*" Australiasian Plant Pathology, vol. 25, pp. 31-35 (1996).
Hamamura, Hiroshi, "Disinfectants containing mepiquat chloride for rice seeds" XP002494120 retrieved from STN Database accession No. 1995:929568.
Fahmy, et al. "Some Factors Affecting the Incidence of Potato Brown Rot" Assiut Journal of Agricultural Sciences (1990) vol. 21(5), pp. 221-230.
Adams, et al. "Transition of Phosphite to Phosphate in Soils" Soil Science (1953) vol. 75, pp. 361-371.
Engelhard, Arthur W. (editor) "Definition of Phosphorus and Potassium" Soilborne Plant Pathogens: Management of Diseases with Macro- and Microelements: APS Press: The American Phytopathological Society, St. Paul, Minnesota, pp. 55-56.
Agrichem Product Sheet for Supa Link, by Agrichem Manufacturing Ind.: Australia, 2 pages (no date).
Agrichem Product Sheet for Supa Stand Phos, published by Agrichem Manufacturing Ind.: Australia, 4 pages (no. date).
Agrichem Product Inforamtion Brochure for "Supa Stand Phos: Supa Crop", subtitled "For the Cotton and Corn Farmer", published by Agrichem Manufacturing Ind.: Australia, 1 page (Oct. 1990).
Agrichem Product Sheet for Supa Crop, published by Agrichem Manufacturing Ind.: Australia, 1 page (no date).
Agrichem, correspondence between Agrichem and Department of Primary Industries, Queensland Government, 24 pages (no date).
Agrichem Product Information Brochure for "Supa Stand Phos: Supa Protective Pop-Up Starter", published by Agrichem Manufacturing Ind.: Australia, 2 pages (Aug. 1990).
Agrichem Product Information Brochure for "Kelpak: Liquid Seaweed Concentrate 'Ecklonia Maxima'", published by Agrichem Manufacturing Ind.: Australia, 1 page (no date).
Agrichem Information Brochure for "Organic Extract: Typical Analysis", published by Agrichem Manufacturing Ind.: Australia, 1 page (no date).
Agrichem Manufacturing Ind., "Water Injection and Foliar Trials 1990/91: Cotton & Maize" published by AGrichem Manufacturing Ind.: Australia, 3 pages, (1990-1991).
Engelhard, Arthur W. "Historical Highlights and Prospects for the Future" Soilborne Plant Pathogens: Management of Diseases with Macro-and Microelements APS Press: The American Phytopathological Society, St. Paul, Minnesota (1989) pp. 9-15.
Alexander, Martin "Introduction to Soil Microbiology" published by John Wiley & Sons, Inc. pp. 352-369 (no date).
Aly, et al. "Effect of Meteorological Factors and Fertilization on Barley Powdery Mildew Infection" Agricultural Research Review (1987) vol. 65(2), pp. 233-242.
Bedi, et al. "Influence of Nitrogen, Phosphorus and Potassium on the Development of Early Blight of Tomato" Indian Phytopathology (1983) vol. 36(3), pp. 546-548.
Biagro Western Sales, S.A. "SPAN, P, P-K, P-K + Copper, P-Zn + Mn, P-Ca" product data sheet; Visalia, CA (no date).
Biagro, S.A. "Metalosate F, Cobre, and S" product data sheet; Valencia, Spain (no date).
Product catalog of Biagro (Bioestimulantes Agricolas, S.A.), a Spanish company, undated but believed to be before Feb. 7, 1993, (with one English translation of all of the fifth page (the page containing Metalosate-F product) and another English translation of only the three Metalosate product on the fifth page).
Bompeix et al., "Modalites de l'obtention des necroses bloquantes sur feuilles detachees de Tomate par l'action du tris-O-ethyl phosphonate d'aluminium (phosethyl d'aluminium), hypotheses sur son mode d'action in vivo," Ann. Phytophathol., 12:4, pp. 337-351, 1980 (French with English translation) (no month).
Bompeix et al., "Mode d'action du phoseethyl al", Phytiatrie-Phytophamacie, 30, pp. 257-272, 1981 (French with English translation) (no month).
Brennan, et al. "Effect of Superphosphate and Superphosphate Plus Flutriafol on Yield and Take-all of Wheat" Australian Journal of Experimental Agriculture (1989) vol. 29(2), pp. 247-252.
Letter from the California Department of Food and Agriculture, Dated Nov. 17, 1993, to Biagro Western Sales, Inc., and attached labeling information.
California Fertilizer Association, "Western Fertilizer Handbook" Soil Improvement Committee, California Fertilizer Association, Horticulture Ed. Interstate Publishers, Danville, Ill. (1990).
Clark, et al. "Fertilizer Trial Using Water Injection Technique with Supracrop Products" Report by D.Q. Clark & Associates Pty. Ltd. (Jul. 1991), 8 pages.
Coffery, et al. "Phosphonates: Antifungal Compounds Against Oomycetes" California Avocado Growers Yearbook, Nitrogen, Phosphorus and Sulphur Utilization by Fungi Symposium of the British Mycological Society (1988), pp. 106-129.
Cook, A. A., "Genetics of Resistance in *Capsicum annuum* to Two Virus Diseases" Phytopathology (May 1960) vol. 50, pp. 364-365.
Cress, Forrest "UCR Phosphite Fertilization Research Could Yield Double Benefit for Avocado Growers", a University of California Newsletter: Division of Agriculture and Natural Resources, 2 pages (no date).
Dabash, et al. "Relation Between Fertilizers and White Rot Disease of Onion with Reference to the Rhizophere" Agricultural Research Review (1985) vol. 63(2), pp. 99-110.
Embleton, et al. "Leaf Analysis Standards" The Citrus Industry: Proc. Int. Soc. Citriculture (1978) pp. 184-186.
Fenn, et al. "Studies on the In Vitro and In Vivo Antifungal Activity of Fosetyl-Al and Phosphorous Acid" Phytopathology (1983), vol. 74, pp. 606-611.
Fenn, et al. "Quantification of Phosphonate and Ethyl Phosphonate in Tobacco and Tomato Tissues and significance for the Mode of Action of Two Phosphonate Fungicides" Phytopathology (1989) vol. 79(1), pp. 76-82.
First Choice Product Sheet for pHortess, published by Western Farm Service, Inc., Fresno, California, 1 page (no date).
Frazier, et al. "Crystallography and Equilibrium Solubility for Ammonium and Potassium Orthophosphites and Hypophosphites" Fertilizer Research (1992) vol. 32, pp. 161-168.
Gottstein, et al. "Induction of Systemic Resistance to Anthracnose in Cucumber by Phosphates" Phytopathology (Aug. 1989) vol. 79, pp. 176-179.
Graham, et al. "Phytophthora Root Rot Development on Mycorrhizal and Phosphorus-fertilized Nonmycorrhizal Sweet Orange Seedlings" Plant Disease (1988) vol. 72(7), pp. 611-614.
Granade, et al. "Increasing Yield and Reducing Disease on Wheat with P and K Fertilization" Better Crops with Plant Food vol. 74(2), pp. 26-27, 30.

McLean, Ben, "The Effects of Nitrogen, Phosphorous, and Potassium Fertilization on Citrus Fruit Quality" (Apr. 1991) found in "Reports for HOS 6412 Nutrition of Horticulture Crops" Vegetable Crops Department Institute of Food and Agriculture Sciences, University of Florida: Review Papers (Spring 1991) by Locascio, Dr. S. J.
Griffith, et al. "Crop Responses at High Soil Test Phosphorus Levels" Better Crops with Plan Food Published by the Potash & Phosphate Institute (PPI) Norcross, Georgia (Fall 1992), 2 pages.
Mattingly, et al. "Progress in the chemistry of Fertilizer and Soil Phosphorus" Topics in Phosphorus Chemistry (1967) vol. 4, pp. 157-290.
Malacinski and Konetzka, "Bacterial Oxidation of Orthophosphite," Journal of Bacteriology, vol. 91, 578-582, (1966).
Gupta, et al. "Effect of Fertilizer Application on Severity of Sooty Stripe of Sorghum (Sorghum bicolor) Caused by Ramulispora sorghi" Indian Journal of Agricultural Sciences (1990) vol. 60(1), pp. 76-77.
Huber, Dr. Don M., "Micronutrients and Plant Disease" Crop Management, Ag Consultant (Feb. 1994).
Huber, D. Don M., "Introduction for: Soilborne Plant Pathogens: Management of Diseases with Macro- and Microelements" Engelhard, Arthur W. (editor): APS Press: The American Phytopathological Society, St. Paul, Minnesota (1989) pp. 1-8.
Karwasra, et al. "Host Nutrition in Relation to Soft Rot Incidence in Potato" Plant Disease Research (1990) vol. 5(2), pp. 170-174.
Lawton, Kirk, "Phosphate Fertilizer in Irrigation Water" Source Unknown (no date) pp. 1532-1533.
Lovatt, Carol J., "A Definitive Test to Determine Whether Phosphite Fertilization Can Replace Phosphate Fertilization to Supply P in the Metabolism of 'Hass' on 'Duke 7'. A Preliminary Report", California Avocado Society 1990 Yearbook, 74, pp. 61-64 (1990) (no month available).
Lovatt, Carol J., "A Definitive Test to Determine Whether Phosphite Fertilization Can Replace Phosphate Fertilization to Supply P in the Metabolism of 'Hass' on 'Duke 7'. A Preliminary Report", 4 pages (1992) (No month available).
Lovatt, "Avocado Research Project Plan and Grant Requirements," a grant proposal presented to the California Avocado Society for fiscal year 1990-1991 (no month).
Lovatt, Carol J. "A Definitive Test to Determine Whether Phosphite Fertilization can Replace Phosphate Fertilization to Supply P int he Metabolism of 'Hass' on 'Duke7'.—a Preliminary Report" Proc. of Second World Avocado Congress (1992), Unknown, Citrograph (1990) vol. 75(7), p. 161.
Lovatt, Carol J., "Foliar Phosphorous Fertilization of Citrus by Foliar Application of Phosphite" Summary of Citrus Research (1990), pp. 25-26.
Lucas et al., "Phosphite Injury to Corn", Agronomy Journal, 71, pp. 1063-1065, 1979 (no month).
MacIntire, et al. "Fertilizer Evaluation of Certain Phosphorus, and Phosphoric Materials by Means of Pot Cultures" Agronomy Journal (Nov. 1950), vol. 42(11), pp. 543-549.
Mahadevamurthy, et al. "Effect of Fertilizer Amendment of Soil and Antagonist Treatment on Sclerotial Germination on Claviceps fusiformis" Plan Disease Research (1990) vol. 5(2), pp. 212-215.
Miyake, et al. "Phosphate Response of Rice in Indonesian Paddy Fields" Technical Bulletin of the Tropical Agriculture Research Center (1984) No. 17, pp. 1-78.
Mohit-Singh, et al. "Effect of Interation of Nitrogen, Phosphorus and Potash on Alternaria Leaf Spot and Fruit Rot of Brinjal" Farm Science Journal (1988) vol. 3(a), pp. 21-23. CAB Abstract.
Mucharromah, et al. "Oxalate and Phosphates Induce Systemic Resistance Against Diseases Caused by Fungi, Bacteria and Viruses in Cucumber" Kentucky Agricultural Experiment Station journal paper (Jul. 1990), 6 pages.
Muchovej et al., "Effect of Exchangeable Soil Aluminum and Alkaline Calcium Salts on the Pathogenicity and Growth of Phytophthora capsici from Green Pepper," Phytopathology, 70, pp. 1212-1214, 1980. (no month).
Mustika, et al. "Control of Pepper Yellow Disease with Fertilizer and Pesticides" Pemberitaan, Penelitian Tanaman Industri Indonesia (1984) vol. 9(50), pp. 37-43.

Nayudu, et al. "Bacterial Spot of Tomato as influenced by Temperature and by Age and Nutrition of the Host" Phytopathology (May 1960) vol. 50, pp. 360-363.
Neilsen, et al. "Response of Fruit Trees to Phosphorus Fertilization" Acta Horticulturae (1990) No. 274, pp. 347-359.
Ouimette, et al. "Comparative Antifungal Activity of Four Phosphonate Compounds Against Isolates of Nine Phytophthora Species" Phytopathology (Feb. 1989) vol. 79(7), pp. 761-767.
PhilomBios DowElanco, "Provide" Product Information Brochure published by PhilomBios DowElanco, Winnipeg, Canada (no date), 8 pages.
Prusky and Keen, "Involvement of Preformed Antifungal Compounds in the Resistance of Subtropical Fruits to Fungal Decay" Plant Disease (1993) vol. 77(2), pp. 114-119.
Rashid, et al. "Effects of Nitrogen, Phosphorus and Sulfur Fertilizer Combinations on the Severity of Alternaria, Drechslera and Bacterial Leaf Blights of Wheat" Bangladesh Journal of Plant Pathology (1985) vol. 1(1) pp. 33-39. CAB Abstract.
Reis, et al. "Effect of Mineral Nutrition on Take-all of Wheat" Ecology and Epidemiology: Phytopathology (1982) vol. 72 (2), pp. 224-229.
Robertson and Boyer, "The Biological Inactivity of Glucose 6-Phosphite, Inorganic Phosphites and Other Phosphites," Archives of Biochemistry and Biophysics, vol. 62, 380-395, 1956.
Robertson, et al. "Orthophosphite as a Buffer for Biological Studies" Archives of Biochemistry and Biophysics (1956), vol. 62, pp. 396-401.
Rothbaum et al., "The Use of Red Phosphorus as a Fertilizer. Part 1. Rates of Oxidation of Red Phosphorus in Soil," New Zealand Journal of Science, 7, pp. 51-66, 1964 (no month).
Rothbaum and Kitt, "The Use of Red Phosphorus as a Fertiliser. Part 2. Extended Studies on Oxidation Rates of Red Phosphorus," New Zealand Journal of Science, 7, pp. 67-74, 1964 (no month).
Widdowson (and Rothbaum) et al., "The Use of Red Phosphorus as a Fertiliser. Part 3. Spot Trials with Perennial Ryegrass and White Clover," New Zealand Journal of Science, 7, pp. 427-455, 1964 (no month).
Rothbaum and Baillie, "The Use of Red Phosphorus as a Fertiliser. Part 4. Phosphite and Phosphate Retention in Soils," New Zealand Journal of Science, 7, pp. 446-451 1964 (no month).
Rothbaum, H.P., "The Use of Red Phosphorus as a Fertiliser. Part 5. The Effect of Copper on the Oxidation Reaction of Red Phosphorus," New Zealand Journal of Science, 8, pp. 388-397, 1965 (no month).
Smilke, et al. "The Mode of Action of Phosphite: Evidence for Both Direct and Indirect Modes of Action on Three Phytophthora spp, in Plants" Phytopathology (1989) vol. 79(9), pp. 921-926.
Sparks, "Growth of Nutrition of Pecan Seedlings from Potassium Phosphate Foliar Sprays" Hort-Science, (1986) vol. 21, pp. 451-453.
Sukarno et al., "The Effect of Fungicides on Vesicular-Arbuscular Mycorrhizal Symbiosis," New Phytologist (1993) vol. (25), pp. 139-147.
Toerlen and Slabbert, "Phosphorous Nutrition of Avocados Through Trunk Injection," Avocado Grower, p. 10, Jan. 1985.
Tsubota, Goro, "Phosphate Reduction the Paddy Field I, Soil and Plant Food," (1959) vol. 5(1), pp. 10-15.
Unknown, "Foliar Applications Do Double Duty" Citrograph (May 1990) vol. 75(7), p. 161.
Unknown, Abstract entitled "Agricola (1970-1978)," (Unknown publication), 1 page, 1992.
Labels for "Resistim," a product of Mandops (UK) Limited, undated but believed to be before Feb. 7, 1993.
Unknown, "Don't Back Away from a Phosphite Confrontation," (unknown publication ), p. 5, Apr. 21, 1992.
Walters, et al. "Induction of Systemic Resistance to Rust in Vicia faba by Phosphate and EDTA: Effects of Calcium" Plant Pathology (1992) vol. 4, p. 444-448.
W.B. McLean & Sons of Clemont Florida, Facsimile Correspondence to Mr. Gurney; (no date), 2 pages.
W.B. McLean & Sons of Clemont Florida, Correspondence to Mr. Lex; (no date), 2 pages.
Wild, Brian, "Enhanced Natural Decay Control in Citrus Fruit" Published by Gosford Horticulture Postharvest Laboratory Gosford, NSW (no date), 7 pages.

Yuda et al, "Search for Efficient Phosphorus Fertilization," Proc. International Society Citriculture, 1981 (no month).

*The Regents of The University of California and Biagro Western Sales, Inc.*, v. *Actagro, LLC*, 2004 U.S. App. Lexis 15663, no month.

*Rhone-Poulenc Agrochime, S.A.*, v. *Biagro Western Sales, Inc.*, 1994 U.S. Dist. Lexis 20754; 35 U.S.P.Q. 2D(BNA) 1203, no month.

*Biagro Western Sales, Inc. and the Regents of The University of California* v. *Grow More, Inc.* 423 F. 3d 1296, CA Fed. (Cal.) 2005, 76 U.S.P.Q. 2d 1347, no month.

Leroux et al., "Vine fungicides and mycotoxins. Laboratory studies of fungicides used on grapewine towards mycotoxin-producing fungi," *Phytoma. La Defense Des Vegetaux*, Ruralia, Boulogne, FR, FR, No. 553, Oct. 1, 2002, pp. 28 to 31.

F. M. Ellner, "Influence of fungicide treatment of deoxynivalenol content in winter wheat artificially infected with *Fusarium culmorum*," *Cereal Research Communications*, vol. 25, No. 3/2, (2997), pp. 735 to 737, Database CA, chemical Abstracts Service, Columbus, Ohio, XP-002494122, Data accession No. 1997:766745.

Chemical Abstracts Service, Columbus, Ohio, XP-002494120, Database accession No. 1995:929568, abstract for JP 7-223913, Hiroshi Hamamura, "disinfectants containing mepiquat chloride for rice seeds."

Homdork et al., "Effects of field application of tebuconazole on yield, yield components and mycotoxin content of *Fusarium*-infected wheat grain,", *Journal of Phytopathology*, 148(1), 1-6, (2000), Database CA, Chemical Abstracts Service, Columbus, Ohio, XP-002494121, Database accession No. 2000-162882.

Japanese Office Action dated May 11, 2010, which issued in the counterpart Japanese Patent Application No. 2004-556910, and an English-language translation thereof.

* cited by examiner

METHODS AND COMPOSITIONS FOR INHIBITING MYCOTOXIN CONTAMINATION IN CEREALS

TECHNICAL FIELD

The present invention relates to a treatment method which intends to reduce contamination amount of mycotoxin produced by plant pathogenic fungi of cereals (hereinafter represented as "DON") in the cereals by using a composition for agri-horticulture containing one or more compounds A selected from the group consisting of ammonium salts, primary to quaternary ammonium salts, alkali metal salts, alkaline earth metal salts and polyvalent metal salts of phosphorous acid and phosphite ester as an active ingredient(s).

BACKGROUND ART

*Fusarium* head blight in cereals frequently occurs in cases of continuous cloudy weather and light rain, and furthermore high temperature from the heading date to the milk-ripe stage (Yukio Ozeki, Hiroshi Sasaki, Yoichi Amano, Hokkaido no Hatasaku Gijutu (Farming Technology in Hokkaido) —Cereals version—, published by Society for Agricultural Technique Propagation, page 209, 1978), and it is a plant disease which causes great damage to cereals in terms of yields, quality and so forth, and can not be avoided in this country due to the high amount of rainfall during the ripening period. As major pathogenic fungi thereof, *Fusarium graminearum, Fusarium culmorum, F. avenaceum* and *Microdochium nivale* have been specified. Although there is difference in occupancy depending on climate conditions and areas, complex infection is often observed in farm fields where the disease has occurred (Kunihei Kishi, Nippon Shokubutsu Byogai Daijiten (Comprehensive Dictionary of Plant Disease in Japan), published by Zenkoku Noson Kyoiku Kyokai (Association for National Farming Village Education), page 74, 1998).

The plant pathogenic fungi which cause this disease produce more than one toxic metabolites referred to as mycotoxin, which contaminates crops during cultivating and poses a risk of ingestion by human and domestic animals through migration to harvestries and processed foods. Researches on mycotoxin in areas such as Europe, North America and East Asia where cultivation of the cereals is active have long history, DON has been specified as a toxic agent whose effects on human and animals are most concerned in terms of both toxicity and the contamination amount, and noticed worldwide. Ingestion of foods contaminated with DON causes acute poisoning where digestive organ symptoms including emesis and diarrhea are major symptoms. In Europe and North America, self-regulating values of DON contamination amount in grains have been established, and the system for intensified surveillance has been organized. While internationally rising momentum in DON surveillance, in 2002 in this country, the Ministry of Health, Labor and Welfare also established an interim standard value of 1.1 ppm for the DON contamination amount in the wheat, and announced that safety of the wheat distributed in the market was assured (Shokuhatu No. 0521001). In relation to the announcement, as an instruction notice for feed safety, the Ministry of Agriculture, Forestry and Fisheries established the interim acceptable value 4.0 ppm for deoxynivalenol in feeds supplied for cattle aged 3 months or more and 1.0 ppm that for domestic animals other than the above (press release). Before DON has been noticed as a fungus producing toxin, people have been protected from healthy risk due to fungous toxin by a law regulation that the contamination ratio of the mixed grains affected with *Fusarium* head blight shall be made less than 1% by visual check at the shipping stage of crude wheat. Thus, in the production fields of the cereals, the damages with *Fusarium* head blight have been reduced and inhibited by giving fungicidal agents effective for pathogenic fungi of *Fusarium* head blight.

Chemicals effective for the pathogenic fungi of *Fusarium* head blight of the cereals commonly used at present are classified into several groups by their action mechanisms and chemical structures of active ingredients (Agricultural Chemical Handbook, 2001 version, published by Nippon Shokubutsu Boeki Kyokai). The SBI agents characterized by inhibition of biosynthesis of sterol universally present as a component of biological membrane of fungi include (RS)-1-p-chlorophenyl-4,4-dimethyl-3-(1H-1,2,4-triazol-1-ylmethyl)pentan-3-ol (common name: tebuconazole), (1RS, 5RS)-5-(4-chlorobenzyl)-2,2-dimethyl-1-(1-H-1,2,4-triazol-1-ylmethyl)cyclopentanol (common name: metconazole), and 1-[2-(2,4-dichlorophenyl)-4-propyl-1,3-dioxolan-2-ylmethyl)-1H-1,2,4-triazole (common name: propiconazole), and they are characterized by having a triazole skeleton in the chemical structures. They have been widely used since they are effective at low doses, rapidly permeate in plant bodies, are resistant to rain and low toxic for flower-visiting insects, and they have a high protection effect on the pathogenic fungi of *Fusarium* head blight of the cereals. Methyl=(E)-2-(2-(6-(2-cyanophenoxy) pyridine-4-yloxy]phenyl)-3-methoxyacrylate (common name: azoxystrobin) and methyl=(E)-2-methoxyimino [α-(o-tolyloxy)-o-tolyl]acetate (common name: kresoxim-methyl) which were developed as strobilurine derivatives which are antimycotic antibiotics and structurally characterised by methoxyacrylate ester are classified into methoxyacrylate type fungicidal agents. The former exerts the protection effect by the inhibition of respiratory activity of the fungi, and the latter does it by the inhibition of cytochrome electron transfer system in mitochondria. The other synthetic fungicidal agents include 1,1'-iminodi(ootamethylene)diguanidium-triacetate (common name: iminoctadine acetate). It is considered as the action mechanism that it causes destruction of a membrane lipid bilayer structure of fungi due to a surfactant-like feature derived from its salt structure. Furthermore, the relevance between the pathogenic fungi and drug efficacy has been researched, and it has been demonstrated that the triazole agents are effective for the 3 species of *F. graminearum, F. culmorum* and *F.* avenaceum, and that the methoxyacrylate agents are effective for *M. nivale*. As mentioned above, occurrence of the disease often accompanies mixture of the multiple pathogenic fungi, and thus, the occurrence of the disease has been protected and inhibited by performing rotation spray with taking advantage of characters of respective agents.

Along with attention for DON, as analysis of its contamination concentration has progressed, it has been being demonstrated that there is no direct relevance between an illness degree of the *Fusarium* head blight and the contamination amount of DON (Rai, G. H., Plattner R and Desjardins A., Relationship between visual scab rating and deoxynivalenol in wheat cultivars, The 1988 National *Fusarium* Head Blight Forum, Chapter 2, pages 21-25). It has been also demonstrated in recent years that *F. graminearum* and *F. culmorum* have DON production capacity but *F. avenaceum* and *M. nivale* do not produce DON. It has been reported that when *M. nivale* is controlled using the methoxyacrylate agent, *F. graminearum* and *F. culmorum* which are antagonized are increased resulting in facilitating the increase of DON contamination amount. Thus, the disease protection only by giving the fungicidal agents can not sufficiently prevent the DON contamination. Furthermore, in the production fields of the cereals, even when the *Fusarium* head blight of the cereals is controlled by combined application of various fungicidal agents, DON is frequently detected at more than 1.1 ppm. This troubles the producers. That is, the DON contamination amount can not be sufficiently reduced only by controlling the pathogenic fungi having a mycotoxin production capacity, which is a conventional technology. Also with respect to fosetyl described in the present statement, the fungicidal effect on the plant pathogenic fungi has been known publicly (U.S. Pat. No. 4,139,616, 1979; and JP 62-87504 A), but there is no mention at all for effects on plants contaminated with mycotoxin. Under such a circumstance, it is an actual state that establishment of a method of substantially reducing the DON contamination amount has been strongly desired in the production fields of the cereals.

The present inventors studied on compositions for agriculture which reduces contamination of wheat with mycotoxin, particularly a DON contamination amount to 1.1 ppm or less or a low contamination amount as possible. As a result, a composition for agri-horticulture developed using one or more compounds A selected from the group consisting of ammonium salts, primary to quaternary ammonium salts, alkali metal salts, alkaline earth metal salts and polyvalent metal salts of phosphorous acid and phosphite ester as an active ingredient(s) has a low controlling effect on pathogenic fungi of *Fusarium* head blight of the cereals but has an excellent contamination inhibitory effect on a mycotoxin contamination, particularly the DON contamination, and have completed the invention.

Also, the inventors have shown a reduction of the DON contamination amount equal to or less than the standard value in mixed use with a fungicidal agent where DON contamination at high concentration of more than the standard value 1.1 ppm has been observed in the mixed use with fungicidal agent for agri-horticulture, and a further inhibitory effect on the DON contamination amount in the mixed use with a fungicidal agent which originally shows a low contamination level, have found an effect where the DON contamination amount is further reduced compared to a single treatment of a fungicidal agent for agri-horticulture, and have completed the invention.

DISCLOSURE OF THE INVENTION

The present invention is a method of reducing the contamination amount of mycotoxin (particularly deoxynivalenol) in cereals characterized in that one or more compounds A selected from the group consisting of ammonium salts, primary to quaternary ammonium salts, alkali metal salts, alkaline earth metal salts and polyvalent metal salts of phosphorous acid and phosphite ester are given to the cereals.

Also, the invention relates to a method of reducing a contamination amount of mycotoxin (particularly deoxynivalenol) in cereals characterized in that a combination of the above compound A is given to the cereals in combination with (suitably as a composition containing both as active ingredients) one or more fungicidal active components for agri-horticulture (hereinafter referred to as the compound B).

BEST MODE FOR CARRYING OUT THE INVENTION

Figure 1:
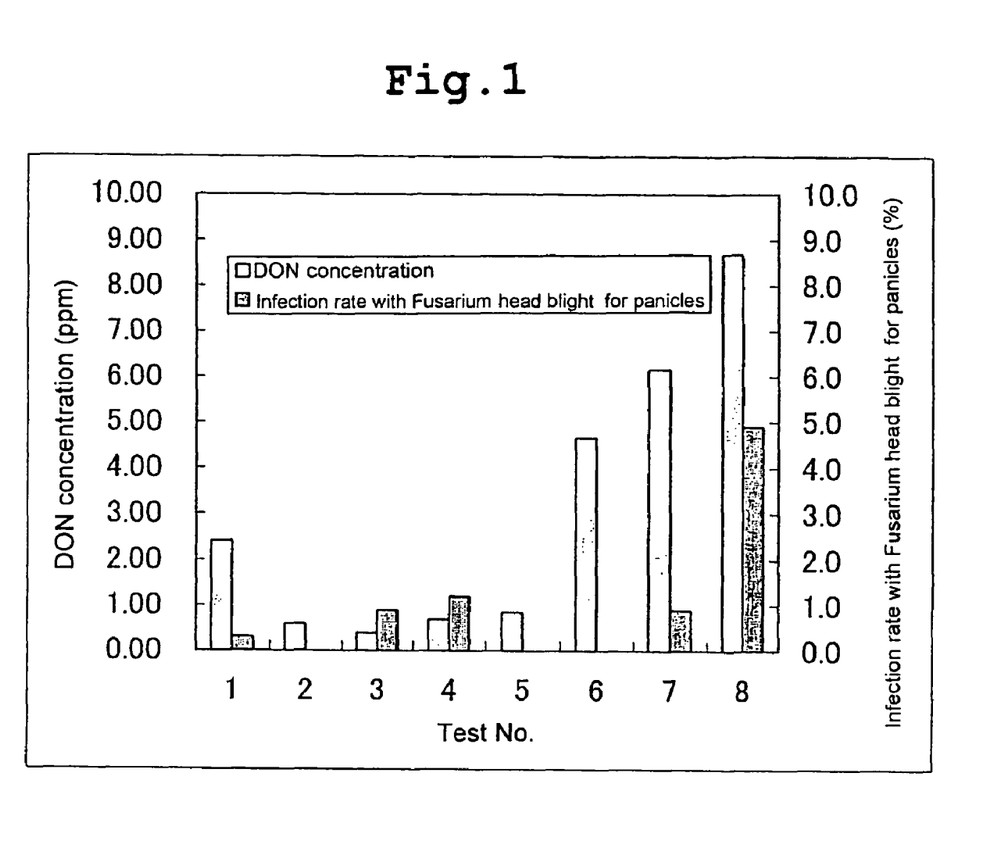
FIG. 1 represents test results of inhibitory effects on DON contamination by phosphite derivatives and alkyl phosphite derivatives (Example 1).
Figure 2:
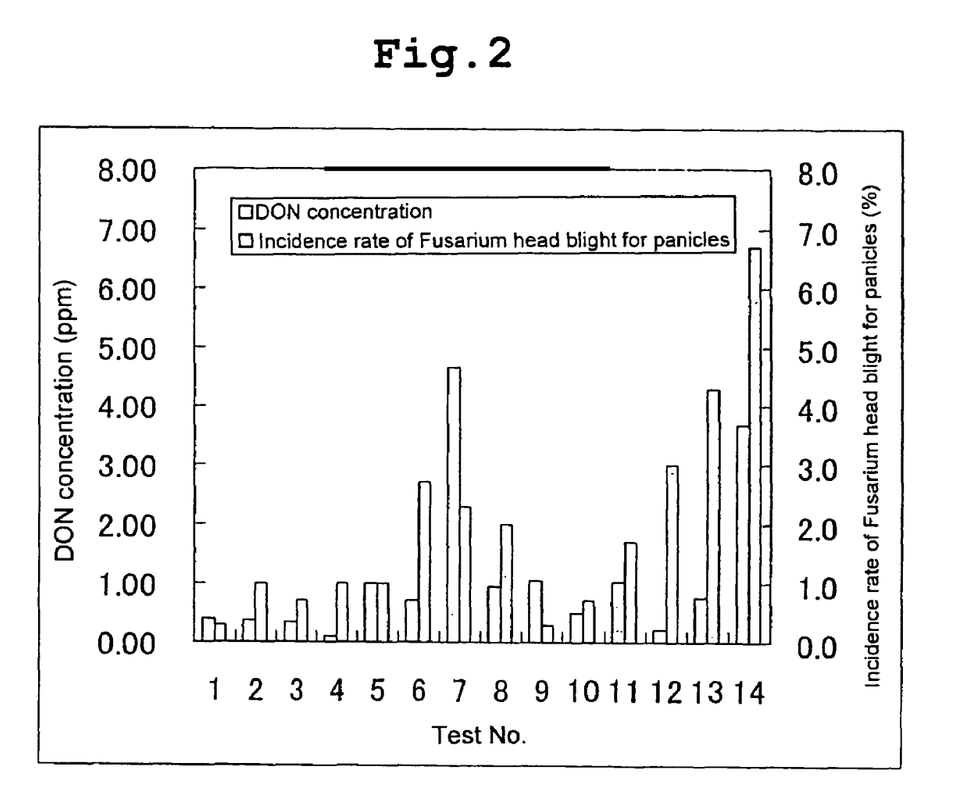
FIG. 2 represents test results of mixed use effects of potassium phosphite with various fungicides (Example 3).

Hereinafter, the invention is described in detail

The ammonium salts, primary to quaternary ammonium salts, alkali metal salts, alkaline earth metal salts and polyvalent metal salts of phosphorous acid and phosphite ester, derived from phosphorous acid are not particularly limited so long as they reduce the contamination with mycotoxin, particularly DON, and for example, include alkali metal salts and polyvalent metal salts of phosphorous acid and phosphite ester, and are suitably potassium phosphite and an aluminium salt (common name: fosetyl) of tris(ethylphosphonate). Methods of assessing the inhibitory effect on mycotoxin contamination, particularly DON contamination in wheat of the invention can includes a method of determining or measuring by comparing a contamination concentration of DON, incidence rate of *Fusarium* head blight for panicles and incidence rate for spikelets in wheat, between a group where a single treatment with phosphorous acid and phosphite ester derivative was given, and a group where a treatment with mixed use of other fungicidal composition was given, and a control group without the treatment with drug, of the wheat cultivated in the field.

It has been confirmed by such a method that the ammonium salts, primary to quaternary ammonium salts, alkali metal salts, alkaline earth metal salts and polyvalent metal salts of phosphorous acid and phosphite ester, derived from phosphorous acid have an excellent inhibitory effect on the mycotoxin contamination, particularly DON contamination, independently on controlling of the pathogenic fungi of the cereals.

The compound B in the invention could be a usual fungicidal active compound for agri-horticulture, and is suitably the fungicidal active compound effective for wheat *Fusarium* head blight, such as a sterol biosynthesis inhibitor (SBI) having a triazole skeleton, azoxystrobin, kresoxim-methyl and iminoctadine.

EXAMPLES

By citing below test examples using potassium phosphite and an aluminium salt (common name: fosetyl) of tris(ethylphosphonate) as the compounds A which are the active ingredients of the invention, the invention is more specifically described, but the invention is not limited thereto.

Example 1

Single Use (±Conventional Control) Effect

Wheat (cultivar: Haruyutaka) was seeded on Apr. 19, 2002, and cultivated according to a conventional cultivating standard (Hokkaido, Agriculture Department, 1995) to establish test sections with 6:75 m$^2$ per section (3 repeats). As the compounds A, potassium phosphite and an aluminium salt (common name: fosetyl) of tris(ethylphosphonate) were given, water solution of 0.038 to 0.120% in P$_2$O$_5$ was prepared, and 100 L per 10 a was sprayed on leaves at next growth stage. That is, the first spray (June 28, flowering date), the second spray (July 8, days after the flowering date, and the third spray. (July 18, 20 days after the flowering date) were performed. A conventional control for the purpose of controlling plant pathogens and plant insects was performed together. That is, the first [June 20, azoxystrobin (2000 times dilution)+fenitrothion (1000 times dilution)), the second [tebuconazole (Jun. 28, 2000 times dilution)+sumithione (1000 times dilution)], and the third [July 8, propiconazole (2000 times dilution)+fenitrothion (1000 times dilution)], the forth [July 17, tebuconazole (2000 times dilution)+fenitrothion (1000 times dilution)] were performed. As controls, the test section where only the conventional control was given and the test section without any control were established. Harvest was performed by harvesting the wheat in 4 m² in the test sections on August 9 (52 days after the heading date). After the harvest, the wheat was applied on a rice grader with 2.2 mm opening of screen to make selected grains, which were then pulverized by a rapid pulverizer to make whole grain powder. The whole grain powder was used as a sample for analysis. The DON contamination concentration was analyzed by ELISA method using commercially available Rida Screen Fast Don supplied from r-Biopharm.

Preparation of Analysis Sample Solutions and Analysis procedure are briefly described.
- To 5 g of the whole grain powder, 100 ml of water was added, and vigorously agitated for 10 min to make a DON extract solution.
- The DON extract solution was centrifuged at high speed, and the supernatant was used for the ELISA analysis.
- According to the method described on ELISA kit, various reagents were added, and subsequently an absorbance of each test solution was measured.
- The DON concentration of each test solution was read out from a standard curve made using DON standard solutions.
- The incidence rate of *Fusarium* head blight for panicles was calculated by counting the number of panicles in 1 m² of each section and the number of diseased panicles included therein.

The results of the present test are shown in Table 1.

TABLE 1

Inhibitory effect of phosphite derivative and alkyl phosphite derivative on DON contamination (2002, Haruyutaka)

| | Treatment | | DON concentration (ppm) | Incidence rate of *Fusarium* head blight for panicles (%) |
|---|---|---|---|---|
| | Active ingredient A | Concentration | Control system | | |
| 1 | Potassium phosphite | 0.038% | Conventional control | 2.41 | 0.3 |
| 2 | | 0.070% | Conventional control | 0.59 | 0.0 |
| 3 | | 0.112% | Conventional control | 0.39 | 0.9 |
| 4 | | | No control | 0.69 | 1.2 |
| 5 | Fosetyl | 0.120% | Conventional control | 0.84 | 0.0 |
| 6 | Potassium phosphate | 0.112% | Conventional control | 4.66 | 0.0 |
| 7 | | | Conventional control | 6.16 | 0.9 |
| 8 | | | No control | 8.69 | 4.9 |

Note)
The concentration of the active ingredient A is the concentration converted into $P_2O_5$.

Note)
The incidence rate of *Fusarium* head blight for panicles was calculated by counting the number of panicles in 1 m² of each section and the number of diseased panicles included therein.

DON was detected at highly contaminated levels which were much higher than the interim standard value, 1.1 ppm that the Ministry of Health, Labor and Welfare had presented from the section with no control and the section with conventional control alone using the fungicidal composition for controlling of *Fusarium* head blight of the cereals. On the other hand, inhibition of DON contamination depending on treated concentrations was observed in the sections treated with potassium phosphite and the aluminium salt (common name: fosetyl) of Tris(ethylphosphonate), and their contamination levels were lower than 1.1 ppm. It is worthy of special mention that even in the section without any control where the conventional control is not performed, the DON contamination concentration is sufficiently reduced by giving potassium phosphite. Furthermore, even when potassium phosphate which is a salt of normal phosphoric acid is given, the DON inhibitory effect is low, and thus it is obvious that the phosphite and alkyl phosphite derivatives play an important role. Even when the incidence rate of *Fusarium* head blight for panicles was at almost the same degree, DON at high concentration was detected in the section without treatment with potassium phosphite. This way, it is evident that the concentration of DON contamination is reduced by the treatment with phosphorous acid and alkyl phosphorous acid and the derivatives thereof.

Example 2

Toxin-Inhibitory Effect by Seeds Diseased with *Fusarium* Head Blight in Example 1

Healthy grains and grains diseased with *Fusarium* head-blight were screened from the crude wheat obtained in Example 1, and the DON contamination concentration of the whole grain powder thereof was analyzed by the ELISA method in the same way as shown in Example 1.

The results of the present test are shown in Table 2.

TABLE 2

DON contamination concentration of grains diseased with *Fusarium* head blight

| | Treatment content | | | DON concentration (ppm) | |
|---|---|---|---|---|---|
| | Active ingredient A | Concentration | Control system | healthy grain | diseased grain |
| 1 | Potassium phosphite | 0.038% | Conventional control | 0.05 | 76.6 |
| 2 | | 0.070% | Conventional control | 0.04 | 44.7 |
| 3 | | 0.112% | Conventional control | 0.04 | 25.4 |
| 4 | | | No control | 0.04 | 75.6 |
| 5 | Fosetyl | 0.120% | Conventional control | 0.96 | 11.0 |
| 6 | Potassium phosphate | 0.112% | Conventional control | 0.06 | 86.9 |
| 7 | | | Conventional control | 1.72 | 90.0 |
| 8 | | | No control | 0.73 | 173.0 |

Note)
The concentration of the active ingredient A is the concentration converted into $P_2O_5$.

Note)
The grains colored with scarlet or orange inherent for *Fusarium* head blight and shrink grains were sorted as the diseased grain, and the grains other than them were sorted as the healthy grains.

The concentration of DON contamination of the healthy grains varied almost within lower range. On the other hand, in the diseased grains with *Fusarium* head blight, DON was detected at an extremely high concentration as expected. However, in the crude wheat determined to be the diseased grains, difference was observed in the concentration of DON contamination. That is, in the section given the treatment with potassium phosphite, the DON contamination concentration was decreased depending on the given concentration of potassium phosphite. This way, it is obvious that giving potassium phosphite reduces the DON contamination concentration in the wheat regardless the presence or absence or the degree of the disease with *Fusarium* head blight of cereals, and further that the reduced degree of the DON contamination depends on the given concentration of potassium phosphite.

Example 3

Mixed Use (1)

Wheat (oultivar: Haruyutaka) was seeded on Apr. 23, 2002, and cultivated according to a conventional cultivating standard (Hokkaido, Agriculture Department, 1995) to establish test sections with 10 m² per section (3 repeats). A suspension containing potassium phosphite and various fungicidal agents was prepared in a liquid mixture made up of a spreading agent (Gramine S: supplied from Hokkai Sankyo Co., Ltd.) and water. Using potassium phosphite as the compound A, 0.070% $P_2O_5$, and the 0.006 to 0.025% fungicidal agent for agri-horticulture for the wheat as the compound B, water solution containing them was prepared, and 100 L thereof per 10 a was sprayed on leaves in the following growth stages. That is, the first spray (June 24, heading date), the second (June 30, flowering stage), the third (July 9) were performed. The harvest was performed on August 12 (50 days after the heading date) by harvesting the wheat in 3.4 m² in each section. After the harvest, the wheat was applied on a rice grader with 2.2 mm opening of. screen to make selected grains, which were then pulverized by a rapid pulverizer to make whole grain powder. The whole grain powder was used as a sample for analysis. The DON contamination concentration was analyzed using HPLC-UV method in officially fixed methods shown by the Minister of Health, Labor and Welfare. Quantitative analysis was performed by repeating three times, and the quantitative value was an average value thereof.

Preparation of analysis sample solutions and the analysis procedure are briefly described.

To 50 g of the whole grain powder, 85% acetonitrile was added, vigorously agitated for 30 min, and subsequently sonicated for 10 min.

After eliminating impurities with filter paper, a filtrate was purified using a pretreatment column MultiSep #227 to make a solution for analysis.

The test solution for analysis was injected into high performance liquid chromatography, and DON was detected by ultraviolet rays.

The DON concentration of each test solution was read out from a standard curve made using DON standard solutions.

The incidence rates of *Fusarium* head blight for Panicles and spikelets were surveyed for 100 panicles in each section.

The results of the present test are shown in Table 3.

TABLE 3

Mixed use effects of potassium phosphite and various fungicidal agents

| | Presence or absence of active ingredient A, potassium phosphite | Active ingredient B, Concentration of active ingredient | DON concentration (ppm) | Incidence rate for panicles (%) | Number of diseased spikelets/panicle |
|---|---|---|---|---|---|
| 1 | X | Tebuconazole | 0.39 | 0.3 | 0.003 |
| 2 | ○ | 0.020% | 0.38 | 1.0 | 0.010 |
| 3 | X | Metconazole | 0.34 | 0.7 | 0.007 |
| 4 | ○ | 0.006% | 0.10 | 1.0 | 0.010 |
| 5 | X | Propiconazole | 1.01 | 1.0 | 0.010 |
| 6 | ○ | 0.017% | 0.72 | 2.7 | 0.027 |
| 7 | X | Azoxystrobin | 4.65 | 2.3 | 0.027 |
| 8 | ○ | 0.010% | 0.96 | 2.0 | 0.023 |
| 9 | X | Kresoxim-methyl | 1.05 | 0.3 | 0.003 |
| 10 | ○ | 0.021% | 0.51 | 0.7 | 0.007 |
| 11 | X | Iminoctadine acetate | 1.04 | 1.7 | 0.017 |
| 12 | ○ | 0.025% | 0.20 | 3.0 | 0.030 |
| 13 | ○ | | 0.77 | 4.3 | 0.050 |
| 14 | Non-treatment | | 3.69 | 6.7 | 0.138 |

Note)
0.07% $P_2O_5$ as potassium phosphite; circle: treated, crisscross: untreated Note)
The incidence rates for panicles and spikelet rates were surveyed for 100 panicles in each test section.

Example 4

Mixed Use (2)

Wheat (cultivar: Haruyutaka) was seeded on May 4, 2003, and cultivated according to a conventional cultivating standard (Hokkaido, Agriculture Department, 1995) to establish test sections with 10 m² per section (3 repeats). A suspension containing potassium phosphite and various fungicidal agents was prepared in a liquid mixture made up of a spreading agent (Gramine S. supplied from Hokkai Sankyo Co., Ltd.) and water. Using potassium phosphite as the compound A, 0.070% $P_2O_5$, and the 0.030 to 0.125% fungicidal agent for agri-horticulture for the wheat as the compound B, an water solution containing them was prepared, and 100 L thereof per 10 a was sprayed on leaves in the following growth stages. That is, the first spray (July 1, flowering stage), the second (July 7), the third (July 14) were performed. Harvest was performed on August 25 by harvesting all wheat in each test section. After the harvest, using a sample divider, the wheat was equally divided, and was applied on a rice grader with 2.2 mm opening of screen to make selected grains, which were then pulverized by a rapid pulverizer to make whole grain powder. The whole grain powder was used as a sample for analysis. The concentration of DON contamination was analyzed by the ELISA method in the same way as shown in Example 1.

TABLE 4

Mixed use effects of potassium phosphite and various fungicidal agents

| | Presence or absence of active ingredient A, potassium phosphite | Active ingredient B, Concentration of active ingredient | DON concentration (ppm) | Incidence rate for panicles (%) | Number of diseased spikelets/panicle |
|---|---|---|---|---|---|
| 1 | X | Tebuconazole | 0.16 | 7.0 | 7.3 |
| 2 | ○ | 0.020% | 0.08 | 5.0 | 5.0 |
| 3 | X | Propiconazole | 0.57 | 4.7 | 5.0 |
| 4 | ○ | 0.017% | 0.11 | 4.7 | 5.0 |
| 5 | X | Azoxystrobin | 0.83 | 4.3 | 4.7 |
| 6 | ○ | 0.010% | 0.50 | 3.7 | 4.0 |
| 7 | X | Trifloxystrobin | 0.35 | 4.3 | 5.0 |
| 8 | ○ | 0.025% | 0.12 | 3.0 | 3.0 |
| 9 | X | Iminoctadine albesilate | 0.22 | 7.3 | 8.0 |
| 10 | ○ | 0.030% | 0.00 | 2.7 | 2.7 |

TABLE 4-continued

Mixed use effects of potassium phosphite
and various fungicidal agents

| | Presence or absence of active ingredient A, potassium phosphite | Active ingredient B, Concentration of active ingredient | DON concentration (ppm) | Incidence rate for panicles (%) | Number of diseased spikelets/panicle |
|---|---|---|---|---|---|
| 11 | X | sulfur | 1.85 | 8.7 | 10.3 |
| 12 | ○ | 0.125% | 0.43 | 8.7 | 8.7 |
| 13 | ○ | | 0.57 | 10.3 | 11.0 |
| 14 | Non-treatment | | 2.15 | 20.4 | 23.8 |

Note)
Potassium phosphite is 0.070% in $P_2O_5$. ○: with treatment, X: without treatment Note)
The incidence rates for panicles and spikelets were surveyed for 100 panicles in each test section.

In the same way as shown in Example 3, in the mixed use with any of the fungicidal agents for agri-horticulture, both the incidence rate for panicle and the incidence rate for spikelet exhibited high values compared to a single treatment, but the DON contamination amount was reduced. Worthy of special mention is the result in section given the single agent treatment with the compound A, where the disease rate of *Fusarium* head blight was high, nonetheless, the DON contamination amount was at a low level.

Example 5

Effects on Fungal Growth and Toxin Production (1)

A water solution containing 5.600% potassium phosphite was prepared, soaked into gas-sterilized wheat seeds of "Hokushin", and subsequently *Fusarium* head blight pathogenic fungus of the cereals, *Fusarium graminearum* having DON production capacity was inoculated, which were then cultured at 27° C. On days 7, 14, 21 and 28 in the culture, the amount of *Fusarium* head blight pathogenic fungus of the cereals and the amount of DON production present in wheat grains were analyzed.

The preparation of ergosterol analysis sample solutions and the analysis procedure are briefly described.

To 5 g of the culture, 80 ml of ethanol was added, and pulverized using a rapid pulverizer.

The ethanol solution containing the pulverized culture was vigorously agitated for 30 min to extract ergosterol.

After eliminating impurities with filter paper, a filtrate was concentrated under reduced pressure, dried, solidified and dissolved again in 10 ml of ethanol to make an analysis sample solution.

The analysis sample solution was injected into high performance liquid chromatography, and ergosterol was detected by ultraviolet rays.

The preparation of DON analysis sample solutions and the analysis procedure are briefly described.

To 4 g of the culture, 80 ml of distilled water was added, and pulverized using a rapid pulverizer.

The water solution containing the pulverized culture was vigorously agitated for 30 min to extract DON.

A part of the extract solution was centrifuged, and the supernatant was used for the ELISA analysis.

According to the instruction manual in the ELISA kit, various reagents were added, and subsequently an absorbance of each test solution was measured.

The DON concentration of each test solution was read out from standard curve made using DON standard solution.

TABLE 5

Change over time of bacterial growth and DON production
in wheat treated with potassium phosphite

| Treatment | Analysis item | Days of culturing | | | |
| | | 7 days | 14 days | 21 days | 28 days |
|---|---|---|---|---|---|
| Potassium phosphite 5.6% | DON (ppm) | ND. | ND. | ND. | ND. |
| | Ergosterol peak area value | 17952 | 115921 | 372377 | 350972 |
| Non-treatment | DON (ppm) | 6.3 | 4.43 | 4.29 | 37.8 |
| | Ergosterol peak area value | 150453 | 271882 | 367236 | 559014 |

Note)
ND means that the analytical value is less than the detection limit (0.222 ppm) of the ELISA analysis kit.

The amount of ergosterol which was an indicator of the amount of fungi was continuously increased during the culture in the non-treatment whereas reached a plateau on the 21st day in the treatment with potassium phosphite. With respect to the amount of DON production, in the non-treatment, the DON production was initiated at an early phase of the culture and remarkably increased on the 28th day. On the contrary, in the treatment with potassium phosphite, DON was not detected during the entire period of the culture. It is obvious that application of potassium phosphite has a high inhibitory effect on the DON production regardless of the presence or absence or the proliferation degree of the fungi for the *Fusarium* head blight of cereals.

Example 6

Effects on Fungal Growth and Toxin Production (2)

A water solution containing 0.056% to 2.800% potassium phosphite was prepared, soaked into gas-sterilized wheat seeds of "Hokushin", and subsequently *Fusarium* head blight pathogenic fungus of the cereals, *Fusarium graminearum* having DON production capacity was inoculated to the wheat seeds, which were then cultured at 27° C. On day 28 in the culture, the amount of *Fusarium* head blight pathogenic fungus of the cereals and the amount of DON production present in wheat grains were analyzed by the methods in the same way as shown in Example 5.

TABLE 6

Effects of potassium phosphite concentration on bacterial
amount of *Fusarium* head blight pathogenic fungus of
the cereals and the amount of DON production

| Treatment concentration | DON (ppm) | Ergosterol peak area |
|---|---|---|
| 0.056% | 1.60 | 1834861 |
| 0.112% | 0.41 | 1769582 |
| 0.28% | ND. | 1810454 |
| 0.560% | ND. | 1921693 |
| 2.800% | ND. | 85891 |
| Non-treatment | 46.1 | 3601748 |

Note)
ND means that the analytical value is less than the detection limit (0.222 ppm) of the ELISA analysis kit.

Considering the amount of ergosterol as the indicator of the amount of fungi, in the treatment with the water solution of 0.056 to 0.560% potassium phosphite, the inhibitory effect on the fungal amount at a moderate degree and similar degree as compared to that in the non-treatment (water only) was observed, and the remarkable inhibitory effect on the fungal amount was observed in the treatment with the water solution of 2.800% potassium phosphite. Concerning DON amount, in the range of concentrations from 0.056 to 2.800% of potassium phosphite in the water solutions, it was significantly lower than that in the non-treatment. It is obvious that the application of potassium phosphite has a high inhibitory effect on the DON production regardless of the presence or absence or the proliferation degree of the fungi for the *Fusarium* head blight of cereals.

INDUSTRIAL APPLICABILITY

According to the invention, it has been demonstrated that an excellent inhibitory effect on mycotoxin contamination, particularly DON contamination can be had regardless of the presence or absence or the degree of the disease with *Fusarium* head blight of cereals although the prevention effect on *Fusarium* head blight pathogenic fungi of cereals is low by spraying one or more compounds A selected from the group consisting of ammonium salts, primary to quaternary ammonium salts, alkali metal salts, alkaline earth metal salts and polyvalent metal salts of phosphorous acid and phosphite ester onto the growing wheat. Also, it has been demonstrated that the contamination amount of mycotoxin is further reduced by the mixed use of the other fungicidal agent for agri-horticulture compared to the use of the single fungicidal agent alone.

The invention claimed is:

1. A method for reducing deoxynivalenol contamination in wheat comprising a step of applying a material consisting essentially of potassium phosphite and optionally at least one fungicidal active ingredient for agri-horticulture selected from the group consisting of tebuconazole, metconazole, propiconazole, azoxystrobin, kresoxim-methyl, iminoctadine acetate, iminoctadine albesilate, trifloxystrobin and sulfur to a seed or plant of wheat wherein the amount of potassium phosphite is sufficient for inhibiting deoxynivalenol production from plant pathogenic fungi in wheat to 1.1 ppm or less, and is 0.56% by weight or less of said material.

2. The method according to claim 1, wherein the at least one fungicidal active ingredient for agri-horticulture is selected from the group of azoxystrobin, iminoctadine acetate and iminoctadine albesilate.

3. The method according to claim 1, wherein the step of applying is to a seed of wheat.

4. The method according to claim 1, wherein the step of applying is to a plant of wheat.

5. The method according to claim 1, wherein the amount of potassium phosphite is 0.112% by weight or less of said material.

* * * * *